US008187580B2

(12) United States Patent
Dykstra et al.

(10) Patent No.: US 8,187,580 B2
(45) Date of Patent: May 29, 2012

(54) POLYMERIC ASSISTED DELIVERY USING SEPARATE ADDITION

(75) Inventors: Robert Richard Dykstra, Cleves, OH (US); Lois Sara Gallon, Finneytown, OH (US); Mannie Lee Clapp, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 906 days.

(21) Appl. No.: 10/695,283

(22) Filed: Oct. 28, 2003

(65) Prior Publication Data

US 2004/0087476 A1 May 6, 2004

Related U.S. Application Data

(60) Provisional application No. 60/423,016, filed on Nov. 1, 2002.

(51) Int. Cl.
*C08L 95/00* (2006.01)
*C09D 5/08* (2006.01)
*A61K 8/00* (2006.01)

(52) U.S. Cl. ................. 424/70.15; 424/70.1; 424/70.11; 512/1; 512/2

(58) Field of Classification Search .................. 512/4, 2, 512/1; 510/101; 424/70.1, 70.11, 70.15
See application file for complete search history.

(56) References Cited

U.S. PATENT DOCUMENTS

| | | | | |
|---|---|---|---|---|
| 3,681,248 | A * | 8/1972 | Gould et al. | 510/438 |
| 4,209,417 | A * | 6/1980 | Whyte | 510/438 |
| 4,318,746 | A * | 3/1982 | Claffey et al. | 106/162.8 |
| 4,326,967 | A | 4/1982 | Melville | |
| 4,339,356 | A * | 7/1982 | Whyte | 512/4 |
| 4,394,127 | A | 7/1983 | Melville | |
| 4,973,422 | A * | 11/1990 | Schmidt | 510/337 |
| 5,120,532 | A * | 6/1992 | Wells et al. | 424/70.15 |
| 5,188,753 | A * | 2/1993 | Schmidt et al. | 510/395 |
| 5,246,603 | A | 9/1993 | Tsaur et al. | |
| 5,302,322 | A * | 4/1994 | Birtwistle | 510/121 |
| 5,556,450 | A * | 9/1996 | Skodell et al. | 106/10 |
| 5,585,092 | A * | 12/1996 | Trandai et al. | 424/65 |
| 5,866,110 | A * | 2/1999 | Moore et al. | 424/70.19 |
| 5,883,058 | A * | 3/1999 | Wells et al. | 510/127 |
| 6,024,943 | A * | 2/2000 | Ness et al. | 424/59 |
| 6,040,282 | A * | 3/2000 | Guskey et al. | 510/119 |
| 6,194,375 | B1 | 2/2001 | Ness et al. | |
| 6,436,421 | B1 * | 8/2002 | Schindler et al. | 424/405 |
| 6,465,420 | B1 | 10/2002 | Perring et al. | |
| 7,056,880 | B2 * | 6/2006 | Wang et al. | 510/515 |
| 2002/0010107 | A1 | 1/2002 | Hoshino et al. | |
| 2002/0058015 | A1 | 5/2002 | Hood et al. | |
| 2002/0065208 | A1 | 5/2002 | Aubay et al. | |
| 2003/0017125 | A1 * | 1/2003 | Rollat et al. | 424/70.1 |

FOREIGN PATENT DOCUMENTS

| | | | |
|---|---|---|---|
| EP | 0 617 051 | A3 | 9/1994 |
| EP | 0 950 070 | B1 | 7/1998 |
| EP | 1 146 057 | A1 | 10/2001 |
| JP | 63 122796 | | 5/1988 |
| WO | WO98/28339 | | 7/1998 |
| WO | WO 98/28339 | A1 | 7/1998 |
| WO | WO98/28396 | | 7/1998 |
| WO | WO 98/28396 | A1 | 7/1998 |
| WO | WO98/28398 | | 7/1998 |
| WO | WO 98/28398 | A1 | 7/1998 |
| WO | WO 99/38944 | A1 | 8/1999 |
| WO | WO 00/59463 | A1 | 10/2000 |
| WO | WO 00/68352 | A1 | 11/2000 |
| WO | WO 01/36577 | A1 | 5/2001 |
| WO | WO 01/79303 | A1 | 10/2001 |
| WO | WO 02/04586 | A1 | 1/2002 |
| WO | WO 02/38713 | A1 | 5/2002 |
| WO | WO 02/50230 | | 6/2002 |
| WO | WO 03/033636 | A1 | 4/2003 |

OTHER PUBLICATIONS

Brookhaven Intruments Corporation, Zeta Potential Theory {http://www.bic.com/Zeta_Theory.html}.*
Liu et al Macromolecules_2002 vol. 35 pp. 6121-6131.*
Brookhaven Instruments ZetaPlus Manual 1994.*
International Journal of Toxicology [Also previously known as Journal of the American College of Toxicology] vol. 1 No. 4 1982, pp. 55-80.*
Marques et al. Journal of the Brazilian Chemical Society vol. 11 No. 6 pp. 592-599.*
Combariza et al Journal of High resolution Chromatography vol. 17 No. 9 pp. 643-646 1994.*
Garcia et al. (J. Soc. Cosmet. Chem. vol. 27 pp. 37-398 1976).*

* cited by examiner

*Primary Examiner* — Patrick Ryan
*Assistant Examiner* — Aaron Greso
(74) *Attorney, Agent, or Firm* — Andrew J. Mueller; Steven W. Miller

(57) ABSTRACT

Benefit agent delivery systems, compositions incorporating such benefit agent delivery systems, and methods for making the delivery system in the compositions are provided. The benefit agent delivery systems of the present invention employ polymer particles having affinities for selected benefit agents, such as perfume, to form the polymeric assisted benefit agent delivery systems, which can effectively deposit benefit agents onto, onto the surface of a substrate, e.g., fabrics being laundered, hard surfaces, hair, skin or nails.

5 Claims, No Drawings

POLYMERIC ASSISTED DELIVERY USING SEPARATE ADDITION

CROSS REFERENCE TO RELATED APPLICATIONS

This application claims priority under 35 U.S.C. §119(e) from Provisional Application Serial No. 60/423,016, filed on Nov. 1, 2002.

FIELD OF THE INVENTION

The present invention relates to polymeric assisted delivery of benefit agents. More particularly, the polymer particles exhibit affinities for selected benefit agents, such as perfume, to form polymeric assisted benefit agent delivery systems, which can effectively deposit benefit agents onto the surface of a substrate, e.g., fabrics being laundered, hard surfaces, hair, skin or nails. The present invention also relates to compositions containing the polymeric assisted benefit agent delivery systems and methods of making the same, preferably by separate addition.

BACKGROUND OF THE INVENTION

It is frequently desirable or advantageous to treat the surfaces of a variety of substrates, such as fabrics, skin, and hair, with benefit agents; exemplary benefit agents include perfumes; flavors; pharmaceuticals or bio-control agents, such as biocides, insecticides, and mildew control agents; and the like.

Products, systems and methods for depositing benefit agents onto the surfaces of substrates are well known in the art. For example, in the context of fabric treatment, including fabric laundering, a variety of laundry and other products exist that can be used to form aqueous washing liquors or rinse baths containing benefit agents; upon contact with the liquors or baths, the benefit agents are deposited onto the fabric. Personal care products also exist that deliver, in a similar manner, benefit agents to substrates, such as skin and hair. These laundry, personal care, and other products can be applied directly to the surface of the substrate as leave-on products or wash-off products. In either product format, the objective of using these products in substrate treatments is to deposit sufficient benefit agents on the substrate surface so that the substrate surface exhibits a residual or longer lasting benefit after treatment of the substrate is completed.

In addition, in many consumer products, it is desirable for certain benefit agents, such as perfume raw materials, to be deposited more effectively on the surface and/or released in a controlled manner over time. Since the most volatile perfume raw materials, referred to as "top notes" are responsible for the "fresh feeling" consumers experience, it is especially desirable for the more volatile top notes to be deposited more effectively and/or released in a controlled manner over an extended period of time.

Since top notes are conventionally lost due to dissolution and/or evaporation in aqueous media, formulators have tried to minimize the loss of top notes by exploring technologies that enhance the deposition of top notes on substrates, even when the substrate is immersed in or treated with copious amount of water and/or when the substrate subsequently is exposed to atmospheric moisture. Even when directly deposited on substrates, there still remains a need to release the perfume raw materials in an extended, controlled manner.

Prior art attempts disclose the use of pre-loaded perfume polymeric particles to aid the deposition of perfume raw materials onto surfaces and/or control the release of perfume from surfaces. Such attempts include matrix systems in which the fragrance is dissolved or dispersed into the polymer matrix, as well as reservoir system in which the fragrance is surrounded by a rate controlling membrane. Other attempts have included polymerizing the perfume raw materials into a polymer particle or absorbing perfume into polymer particles. These systems are "pre-loaded perfume polymeric particles". Details of these attempts are described in U.S. Pat. No. 6,149,375; WO 98/2839; WO 00/68352; WO 01/79303 and EP 925,776.

Formulators have been less than successful in efficiently depositing perfume raw materials, especially top notes, onto substrates using pre-loaded perfume polymeric particles. Without being bound by theory, the lack of efficiency can be due to reduction or loss of the interaction between the benefit agent and the delivery system during in-product storage. For example, the interaction between perfume and polymer particle can be lost via uncontrolled diffusion of perfume raw material from the pre-loaded perfume polymeric particles into the product matrix or atmosphere. Such loss is quite common under the storage conditions consumer products typically experience.

Attempts to stabilize the pre-loaded perfume polymeric particles to in-product diffusion have resulted in limited success. Attempts to increase stability can be accompanied by undesirable changes in the rate of release of the benefit agent from the delivery system.

Notwithstanding the advances in the art, there remains a continuing need for better benefit agent delivery systems, especially those delivery systems that are effective for delivering residual and long-lasting benefit agents to substrates treated with such delivery systems.

SUMMARY OF THE INVENTION

One aspect of the present invention relates to a benefit agent delivery system suitable for delivering a benefit agent to a substrate, the benefit agent delivery system comprising a polymer particle and a benefit agent, wherein the polymer particle and the benefit agent are separately added to a matrix to form the benefit agent delivery system; and when the benefit agent delivery system is deposited onto the substrate, directly or indirectly, the Response Factor (RF) exhibited by the benefit agent delivery system is at least about 1.5.

Another aspect of the present invention relates to method for making a granular or liquid composition containing a benefit agent delivery system comprising the steps of:

a) providing a granular or liquid matrix;

b) adding a polymer particle to the matrix; and c) adding a benefit agent to the matrix;

wherein the polymer particle and benefit agent are added as separate, discrete components from different sources to form the benefit delivery system.

The present invention also relates to the composition comprising the polymeric assisted benefit agent delivery systems.

DETAILED DESCRIPTION OF THE INVENTION

Definitions

As used herein, "separate addition" means that the perfume and the preformed polymer particles are separately added to and mixed in a matrix or medium containing adjunct ingredients to form the perfume polymeric particles in the final product/composition. In other words, the perfume and the polymer particles are not pre-mixed in a carrier solvent to form the perfume polymeric particles prior to being added to the a matrix or medium containing adjunct ingredients to form the final product.

As used herein, "different sources" means different containers, different conduits, different compartments of a container or a conduit, and the like, so long as the polymer particles and benefit agents do not come into contact with one another prior to being added to the matrix.

As used herein, "non-polymerically associated" means that the benefit agent is absorbed in, adsorbed on or otherwise associated with the polymer after the polymer has been formed. In other words, the benefit agent is not present with the polymer during polymerization or melting of the polymer, rather, the benefit agent is mixed with preformed polymer particles to produce a benefit agent delivery system. For purposes of the present invention, this definition excludes encapsulation wherein a polymer encapsulates a perfume.

"Benefit agent delivery system" or "delivery system" comprises a benefit agent and a polymer particle, which are combined in such a manner as to (i) enhance or increase the deposition of benefit agent onto a substrate and/or (ii) increase or prolong the release of benefit agent from a substrate after said substrate has been exposed to said benefit agent delivery system. Benefit agent delivery systems can be incorporated into a product composition, which may comprise optional adjunct ingredients. Such product composition include, but are not limited to, personal care/cleansing products, fabric care/cleaning products, hard surface care/cleaning products.

As used herein, "adjunct ingredients" means those formulation ingredients that are used in the end product compositions. Such adjunct ingredients are not intended to be those ingredients used in the process of producing the polymer particles that form the basis of the benefit agent delivery system of the present invention, such as processing aids and/or stabilizing agents.

As used herein, "directly applied", "direct applications" or "delivering directly" means that a benefit agent is applied to a substrate via a composition containing the benefit agent delivery system such that the benefit provided by the benefit agent is realized and/or recognized prior to or without subsequent dilution. That is, the benefit agent delivery system can be formulated into a composition that is used as a leave-on product, which is applied to the substrate without dilution or rinse off. For example, the benefit agent delivery system or the product composition containing it is sprayed onto a substrate and/or wiped on to a substrate, rather than having the benefit agent delivery system or the product composition containing it contact or deposit indirectly onto a substrate from a dilute solution (i.e., wash liquor). Nonlimiting examples include fine fragrance perfume applications or products; home care perfume products, such as freshening compositions that are typically applied to upholstery, carpets and other fabric articles; hard surface treating products; beauty care products, such as creams, lotions, deodorants, antiperspirants, and other topical compositions; hair care products, such as hair spray, leave-in conditioners, and the like.

As used herein, "indirectly applied", "indirect applications" or "applied indirectly" means that the substrate is contacted with a dilute solution of the benefit agent delivery system or a product composition containing it, such as in an aqueous solution or dispersion of such a delivery system or product composition. For purposes of this invention, a "dilute solution" of the delivery system or product composition is a solution that contains a concentration of the benefit agent that is at least about 10%, preferably at least about 30%, more preferably at least about 50% lower than the concentration of the benefit agent in the delivery system or product composition prior to such dilution. Such dilute solutions or dispersions can, of course, be formed by diluting the delivery system or the product composition containing it, with water. For example, a laundry detergent containing a perfume delivery system is diluted with water and the dilute solution is used as the wash liquor or bath for laundering fabric articles.

Indirect application also includes the situation where a substrate is initially contacted with the concentrated delivery system-containing product and subsequently diluted/rinsed. For example, even though a shampoo or body wash product may initially be contacted with and applied directly to hair or skin, such products are quickly diluted by the addition of water and used thereafter as an indirect application of the benefit agent delivery system. It is understood that for the indirect application, there must be sufficient contact between the substrate and the delivery system to deposit at least some measurable amount of the benefit agent onto the surface before dilution or rinse takes place. Such contact time can range from about 5 seconds to about 30 minutes, preferably from about 15 seconds to about 15 minutes, and more preferably from about 30 seconds to about 5 minutes.

For purposes of this invention, an aqueous solution or dispersion of a delivery system or product composition may contain no more than about 5000 ppm, preferably no more than about 500 ppm, more preferably no more than about 50 ppm, and most preferably no more than about 10 ppm. In some embodiments, a dilute solution of the delivery system or product composition may even contain no more than about 1 ppm, of the benefit agent.

Benefit Agent Delivery System

The present invention provides a benefit agent delivery system suitable for delivering a benefit agent to a substrate, wherein the benefit agent delivery system comprises a benefit agent and a polymer particle such that when the polymer particle and the benefit agent are directly or indirectly applied to a substrate, the benefit agent provides a benefit to the substrate that is more intense and/or for a longer period of time than when the benefit agent is delivered to the substrate without the polymer particle being present.

The enhancement provided by the present benefit agent delivery system may be shown in the amount of benefit agent deposited onto the substrate surface or in the amount of benefit agent released from the substrate surface. The enhancement may also be shown in the type of benefit agent that is difficult or impossible to be delivered to the substrate by other delivery methods or delivery vehicles, specifically the type of benefit agents that tend to have higher affinity for the product matrix than for the substrate surface, and/or the type of benefit agent that is easily washed away from the substrate surface during the rinse process.

Further, enhancement is shown when the benefit agent delivery system is applied, directly or indirectly, to a substrate, the benefit agent provides a benefit to the substrate for a longer period of time than when the benefit agent is delivered to the substrate without the polymer particle being present.

Contrary to the general notion that the polymer particles and the benefit agents should be pre-mixed (i.e., when both are present in high concentrations in a carrier solvent) before the pre-mix is added to the product matrix or medium, it is surprising to discover that when the polymer particle and the benefit agent are separately added as discrete components to the product matrix (e.g., a granular or liquid matrix) they are also effective in forming a benefit agent delivery system, which imparts enhanced and/or prolonged benefit to the surface of a substrate. Without being bound by theory, it is believed that the polymer particle and the benefit agent can be selected/paired for their selectivity or affinity for each other such that the polymer particle and the benefit agent can become associated even when they are diluted by the product matrix and in the presence of adjunct ingredients.

Moreover, because of the selectivity or affinity between the benefit agent and the polymer particle, they can be separately added to a diluted, and preferably an aqueous, solution or dispersion of the product composition and still able to form the benefit agent delivery system that delivers the enhanced and/or prolonged benefit to a substrate surface. Additionally, the benefit agent and polymer particle can be applied onto the substrate surface in separate, undiluted solution or dispersion and still able to form the benefit agent delivery system that delivers the enhanced and/or prolonged benefit to a substrate surface.

It is also discovered that regardless of the sequence in which the polymer particles and the benefit agents are added to the matrix, the resulting benefit agent delivery system, made by the separate addition mode (i.e., not by the pre-mix mode), would impart enhanced benefit to the substrate surface.

In one embodiment, the polymer particle is introduced into the product matrix or composition via a source that is different from the source that introduces the benefit agent. In another embodiment, the polymer particle is introduced into the product matrix before, after or simultaneously with the benefit agent. In yet another embodiment, the polymer particle and the benefit agent are separate, discrete components at least one point in time after the product or composition has been produced and become associated with one another prior to, during or as result of being applied, directly or indirectly, to a substrate.

In a specific embodiment of the present invention, the benefit agent is a perfume raw material, preferably a perfume raw material having a Kovats Index (KI) less than about 1700, and more preferably a perfume raw material having a Kovats index from about 1000 to about 1400. The "Kovats Index" is a term known in the perfume industry. All KIs disclosed herein are determined using polydimethylsiloxane as the non-polar stationary phase in the column (referred to as a "DB-5 column").

In liquid matrices, especially, on a weight basis, the ratio of polymer particle to benefit agent can vary widely, and will frequently range from about 1000:1 to about 1:50. In one embodiment, the ratio of polymer particle to benefit agent is from about 1000:1 to about 1:5, more typically from about 100:1 to about 1:2, even more typically from about 50:1 to about 1:1.

In one embodiment of the present invention, the polymer particle is present in the final composition at a level of about 0.002 to about 10%, more preferably from about 0.05 to about 5% by weight of the composition.

In another embodiment of the present invention, the benefit agent is present in the final composition at a level of from about 0.001 to about 10%, preferably from about 0.01 to about 5% by weight of the composition.

Liquid or Granular Matrix

The benefit agent delivery systems can be incorporated into a liquid matrix to form the end product. The term "liquids", as used herein, includes fluids as well as gels and foams. The liquid matrix may be aqueous or non-aqueous, wherein water is typically the major component of the aqueous matrix and conventional organic solvents (e.g., lower alcohols) may be used to form the matrix for the non-aqueous matrix. Liquid products, i.e., those containing about 10% or greater of water or other solvents, are typical for the present invention.

The benefit agent delivery systems can be incorporated into a granular matrix. The term "granular matrix", as used herein include which any type of solid material, including porous and non-porous particles, powders or sponges that can be fashioned into agglomerates, tablets, sheets, and the like. In some embodiments, the granular matrix comprises particles or granules ranging in size from about 1 μm to about 100 mm. The granular matrix may further comprise either inert or active ingredients, or both.

The liquid or granular matrix used to form the delivery systems herein can comprise one or more adjunct ingredient, such as surfactant, polymer additive, deposition polymer, thickener, etc., either in the presence or absence of water. In the case where there is no water, the adjunct ingredient can serve as the matrix.

The polymer particles and benefit agents can be separately added to the liquid or granular matrix to form an end product containing the delivery system of this invention. Examples for the end product include, but are not limited to, liquid or granular detergent composition for laundry or hard surface cleaning; personal care composition for hair or skin cleaning or maintenance.

Separate Addition of Polymer Particle and Benefit Agent

As discussed above, it is advantageous to have the polymer particle and the benefit agent added separately to the liquid or granular matrix. Thus, the polymer particle and the benefit agent may be added to the matrix at separate times, or from separate containers and/or conduits, or from separate holding or delivery means.

In another embodiment of the separate addition method, the polymer particle and the benefit agent may be separately prepared or mixed with carrier fluids or portions of the matrix, then the pre-dispersions or mixtures are combined to form the benefit agent delivery system in the end product. For example, the polymer particle or the benefit agent can be separately added to the matrix in the form of a concentrate or an aqueous dispersion, wherein each concentrate or dispersion comprises at least about 50 wt % of the polymer particle or the benefit agent.

In still another embodiment of the separate addition method, the polymer particle and the benefit agent may even be mixed together prior to combination with the matrix so long as substantially no chemical interaction occurs between these materials prior to their contact with the matrix.

In a further embodiment of the separate addition method, the polymer particle is added to a fully formulated, perfume-containing product.

Additional adjunct ingredients can be added to the matrix at any time. The adjunct ingredient can also serve as the matrix into which the polymer particle and benefit agent are incorporated.

Encapsulation, referring to the structure where a polymer physically surrounds a benefit agent, is excluded from the benefit agent delivery system of the present invention. An example of encapsulation is the physical relationship exhibited by cyclodextrin and perfume. However, the polymer particle of the invention may encapsulate material that is not among the benefit agents disclsoed herein. Furthermore, polymer may be heated to its melting point and a perfume is added to the melt before cooling. These structures are outside the scope of the benefit agent delivery system of the present invention.

Polymer Particle

The polymer particle of the present invention is polymerized from at least one cationic monomer and one or more non-cationic monomers, preferably also a cross-linking monomer. The polymerization process may be any suitable process known in the art, such as emulsion, suspension or mini-emulsion polymerization. During the polymerization, an emulsifier or stabilizer may be present to keep the polymer particles from coagulating, crashing and/or settling out of the aqueous solution in which the polymer particles are being formed.

The monomers of the polymer particle may be selected such that the resulting polymer particle has an affinity for perfume raw materials having a molecular weight of less than about 200, a boiling point of less than about 250° C., a ClogP of less than about 3, or a Kovats Index value of less than about 1700, preferably from about 1000 to about 1400.

The polymer particle can be derived from about 50% to about 100%, preferably from about 60 to about 95% by weight of non-cationic monomers; from about 0% to about 50%, preferably from about 0% to about 10% by weight of cationic or anionic monomers; and from about 0% to about 25%, preferably from about 1% to about 10% by weight of cross-linking monomers. The monomers polymerized to form the polymer particle may be used in a weight ratio of non-cationic monomer:cationic monomer:cross-linking monomer of from about 10:0.02:0 to about 5:2.5:1.

The polymer particles may be in the form of micro-particles or nanoparticles having an average particle size of from about 100 nm to about 50 μm, as measured by light scattering using Brookhaven Particle size analyzer or Horiba particle size analyzer. In one embodiment, the polymer particle may have an average particle size of from about 1 μm to about 39 μm, preferably from about 3 μm to about 20 μm and more preferably from about 5 μm to about 12 μm. In another embodiment, the polymer particle may have an average particle size of from about 100 nm to about 1 μm, preferably from about 200 nm to about 900 nm and more preferably from about 700 nm to about 900 nm.

In one embodiment, the polymer particles have a glass transition temperature, Tg, from about 50° C. to about 150° C., preferably from about 80° C. to about 120° C.

In one embodiment, the polymer particle may comprise a single polymer after polymerization of the monomers. In another embodiment, the polymer particle may comprise two or more polymers, which are produced by the reaction (e.g., grafting) between the emulsifier or stabilizer and the polymerizing monomers or resulting polymer particle. For example, the polymer particle may comprise a first polymer resulting from the polymerization of the monomers, and a second polymer grafted or associated with the first polymer, such as polystyrene and poly(methyl methacrylate-dimethyl amino ethyl methacrylate) copolymer.

It is desirable that the polymer particle is stable in aqueous dispersions. It is also desirable that the polymer particle is stable within product formulations, such as perfume compositions or fabric softener compositions that contain laundry adjuncts, fabric softeners, and the like.

Stability of the polymer particle can be influenced by factors such as the average particle size of the resulting polymer particle, the net charge of the resulting polymer particle, the interactions or compatibility between the polymer particles and other ingredients in the compositions, such as emulsifiers or stabilizers.

In one embodiment, the polymer particle has a net cationic charge about 20 mV to about 80 mV, preferably from about 30 mV to about 50 mV and more preferably from about 35 mV to about 45 mV, as measured by a Brookhaven zeta potential analyzer.

To aid in the stabilizing the polymer particle in aqueous dispersions and/or in product formulations, such as perfume compositions, a stabilizer, also known as a colloidal stabilizer may be added to the aqueous dispersion and/or product formulation. It is desirable that the colloidal stabilizer be compatible with other ingredients within the aqueous dispersion and/or product formulation.

The polymer particle may be water-insoluble. In other words, when added to water, the polymer particle physically separates from the water (i.e. settles-out, flocculates, floats) within 5 minutes after addition, whereas a material that is "soluble in water" does not physically separate from the water within 5 minutes after addition. Another way of describing water-insoluble materials for purposes of the present invention is the fact that water-insoluble materials are not soluble in distilled (or equivalent) water, at 25° C., at a concentration of greater than about 5%, preferably greater than about 3% and more preferably greater than about 1% by weight of the mixture containing water and polymer particles.

The polymer particle may have a weight-average molecular weight of from about 1,000 to about 2,000,000 preferably from about 5,000 to about 1,000,000, more preferably from about 10,000 to about 750,000, more preferably from about 20,000 to about 500,000 daltons. The weight-average molecular weight of the polymer particle, can be determined via conventional methods such as gel permeation chromatography.

A. Non-Cationic Monomer

The non-cationic monomer may be a hydrophobic group-containing monomer. Examples of the hydrophobic group include, but are not limited to, alkyls, cycloalkyls, aryls, alkaryls, aralkyls and mixtures thereof.

The non-cationic monomer may be a hydroxyl-containing monomer, an anionic group-containing monomer, or a zwitterionic monomer. The non-cationic monomer include, but are not limited to, ethylene glycol phenyl ether acrylate (EG-PhA), trans-cinnamic acid, 2-ethyl hexyl acrylate, and mixtures thereof.

Nonlimiting examples of suitable non-cationic monomers include, but are not limited to, methyl methacrylate, methyl acrylate, ethyl acrylate, n-propyl acrylate, iso-propyl acrylate, n-butyl acrylate, isobutyl acrylate, hydroxyethyl acrylate, hydroxypropyl acrylate, benzyl acrylate, ethylhexyl acrylate, n-propyl methacrylate, ethyl methacrylate, iso-propyl methacrylate, isobutyl methacrylate, n-butyl methacrylate, methacrylic acid, acrylic acid, acrylamide, methacrylamide, styrene, α-methyl styrene, hydroxyethyl methacrylate, hydroxypropyl methacrylate, hydroxybutyl acrylate, hydroxybutyl methacrylate, PEG acrylate, phenyl methacrylamide, t-butyl methacrylamide, p-hydroxyphenyl methacrylamide, vinyl ethers, vinyl ketones, vinyl acetates, vinyl phenols, acylamido-2-methylpropanesulfonic acid, vinlysulfonate, vinylpropionate, methylallylsulfonic acid, N-vinyl formamide and N-vinylpyrrolidone.

B. Cationic Monomer

The cationic monomer of the present invention comprises a cationic unit. For the purposes of the present invention the term "cationic unit" is defined as a moiety which when incorporated into the structure of the polymer particle of the present invention, is capable of maintaining a cationic charge within the pH range of from about 2 to about 8. The cationic unit is not required to be protonated at every pH value within the range of about 2 to about 8. Non-limiting examples of units which comprise a cationic moiety include the cationic units having the formula:

[I]

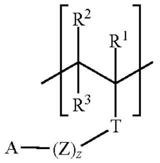

wherein each of $R^1$, $R^2$ and $R^3$ are independently selected from hydrogen or $C_1$ to $C_6$ alkyl, and preferably hydrogen, $C_1$ to $C_3$ alkyl, more preferably, hydrogen or methyl; T is a substituted or unsubstituted, saturated or unsaturated, linear or branched moiety selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, carboalkoxy, and mixtures thereof; Z is a moiety selected from the group consisting of: $-(CH_2)-$, $(CH_2-CH{=}CH)-$, $-(CH_2-CHOH)-$, $(CH_2-CHNR^4)-$, $-(CH_2-CHR^5-O)-$ and mixtures thereof, preferably $-(CH_2)-$, wherein $R^4$ and $R^5$ are independently selected from hydrogen or $C_1$ to $C_6$ alkyl, preferably hydrogen, methyl, ethyl; z is an integer from 0 to 12, preferably from 2 to 10, more preferably from 2 to 6; A is $NR^6R^7$ or $NR^6R^7R^8$, wherein each of $R^6$, $R^7$ and $R^8$ are independently selected from H, $C_1$-$C_8$ linear or branched alkyl, or alkyleneoxy having the formula:

$$-(R^9O)_yR^{10}$$

wherein $R^9$ is $C_2$ to $C_4$ linear or branched alkylene or carbonyl alkyl; R10 is hydrogen or $C_1$ to $C_4$ alkyl,; y is from 1 to about 10. In one embodiment, $R^6$, $R^7$ and $R^8$ are independently, hydrogen, $C_1$ to $C_4$ alkyl. Alternatively, $NR^6R^7$ or $NR^6R^7R^8$ can form a heterocyclic ring containing from 4 to 7 carbon atoms, optionally containing additional hetero atoms, optionally fused to a benzene ring, and optionally substituted by $C_1$ to $C_8$ hydrocarbyl, or acetates. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred.

Nonlimiting examples of suitable cationic monomers for the present invention include, but are not limited to, dimethylamino alkyl acrylates, especially dimethylaminoethyl methacrylate, vinyl pyrrolidones, vinyl imidazoyls, vinyl ethers having dialkyl amino groups, vinyl pyridines, alkyl acrylamides, dialkylamino alkyl acrylamides, and amino alkyl acrylamides.

C. Cross-Linking Monomer

The cross-linking monomer may be present in the polymer particle of the present invention. Nonlimiting examples of suitable cross-linking monomers include, but are not limited to, diacrylate, dimethacrylate, diethylene glycol diacrylate, divinylbenzene, divinyl ether, ethylene glycol dimethacrylate, pentaerythritol triacrylate, polyallyl sucrose, trivinyl benzene, divinyl toluene, trivinyl toluene, triethylenglycol dimethacrylate, tetraethylenglycol dimethacrylate, allylmethacrylate, diallylmaleate, triallylmaleate and 1,4-butanediol diacrylate, triallylmaleate 1,2-ethanediol diacrylate, 1,3-propanediol diacrylate, 1,6-hexanediol diacrylate, divinyl bezene, and ethylene glycol diacylate.

D. Emulsifier or Colloidal Stabilizer

Suitable emulsifiers and/or colloidal stabilizers for use in the present invention are known in the art. Nonlimiting examples of such emulsifiers or colloidal stablizers include, but are not limited to, ricinolyamidopropyltrimethyl-ammoniummetho sulfate, cocopentylethoxymethyl-ammoniummethyl sulfate, cocobis(2-hydroxyethyl) methylammonium chloride, cetyltrimethylammonium bromide, cetylpyridinium chloride, glyceryl stearate, stearadamidoethyl diethylamine, ethoxylated oleylamines, ethoxylated fatty amines, ethoxylated quaternised fatty amines, ethoxylated fatty alcohols, sorbitan stearate, polysorbate, stearate, sodium dodecyl sulfate, ammoniumnonoxynol sulfate, dodecyltrimethyl ammonium bromide, sodium lauryl sulfate, sodium laurate, gelatine, polyvinylalcohol, aminomethylated starch, poly(vinylalcohol-co-vinylacetate) copolymers, modified cellulose like carboxymethyl cellulose, methyl cellulose, hydroxyethyl cellulose, polyoxyethylene, polyvinylpyrrolidone, polyoxyethylene-polyoxypropylene-polyoxyethylene copolymers, polyether-modified dimethicones and polyether-alkyl-dimethicones copolymers, cationic silicones and polyimides.

A colloidal stabilizer may be used to maintain particle dispersive stability, particularly of larger sized particles. Suitable colloidal stabilizer include, but are not limited to, propylene oxide-ethylene oxide copolymers or ethyleneoxide-propylenoxide graphted polyethylenimines, polyoxyethylene (X) isooctylphenyl ether where X is an integer from 20 to 80, fatty alcohol ethoxylates, polyethoxylated polyterephthalate block co-polymers polyvinylpyrrolidone polyvinylpyrrolidone and copolymers containing vinylpyrolidone.

E. Initiators

Suitable initiators for use in the polymerization process of the present invention are known in the art. Examples include, but are not limited to sodium persulfate and azo initiators such as 2,2'-azobis(2-methylpropionamide)dihydrochloride; 2,2'-azobis(2-amidinopropane)dihydrochloride; 2,2'-azobis(N,N'-dimethyleneisobutyramidine)dihydrochloride; 2,2'-azobis(2-methylbutyronitrile; 2,2'-azobis(4-methoxy-2,4dimethylvaleronitrile; and 2-(Carbamoylazo)-isobutyronitrile.

Benefit Agents

The benefit agents suitable for use in the benefit agent delivery system of the present invention include, but are not limited to, flavor ingredients, pharmaceutical actives, biocontrol actives, perfume raw materials, and mixtures thereof. In some embodiments of the present invention, the benefit agents can be volatile materials, such as perfume raw materials or topnotes. For the purpose of the present invention, a volatile material refers to a material having a boiling point of less than about 250° C.

Flavor ingredients include spices or flavor enhancers, which contribute to the overall flavor perception of the product into which the benefit agent delivery system is incorporated. Pharmaceutical benefit agents include drugs. Biocontrol agents include biocides, antimicrobials, bactericides, fungicides, algaecides, mildewcides, disinfectants, sanitizer-like bleaches, antiseptics, insecticides, insect or moth repellant, vermicides, plant growth hormones, and the like. Typical antimicrobials include glutaraldehyde, cinnamaldehyde, and mixtures thereof. Typical insect or moth repellants are perfume ingredients, such as citronellal, citral, N,N-diethyl meta toluamide, Rotundial, 8-acetoxycarvotanacenone, and mixtures thereof.

The preferred benefit agent used to form the delivery systems of this invention is perfume or perfume raw material. A typical disclosure of suitable perfume raw materials, traditionally used in perfumery, can be found in "Perfume and Flavor Chemicals", Vol. I and II, S. Arctander, Allured Publishing, 1994, ISBN 0-931710-35-5. Perfume top notes having a Kovats Index of less than 1700 are most preferred benefit agents for use in the delivery systems of this invention.

Adjunct Ingredient

Suitable adjunct ingredients include, but are not limited to, surfactants, builders, chelating agents, dye transfer inhibiting agents, dispersants, enzymes, and enzyme stabilizers, catalytic metal complexes, polymeric dispersing agents, clay soil removal/anti-redeposition agents, brighteners, suds suppressors, dyes, perfumes, structure elasticizing agents, fabric softeners, viscosity modifiers, carriers, hydrotropes, processing aids and/or pigments. In addition, suitable examples of such other adjuncts and levels of use are found in U.S. Pat. Nos. 5,576,282, 6,306,812 B1; 6,326,348 B1; PCT Patent Application Nos. WO 00/02982 and WO 00/02987.

Other adjunct ingredients suitable for use in personal care compositions include, but are not limited to, aesthetic agents and other active agents. For example, the compositions may include absorbents, abrasives, anticaking agents, antifoaming agents, antimicrobial agents binders, buffering agents, bulking agents, cosmetic biocides, conditioning agents, deposition polymers, film formers, plasticizers, preservatives, preservative enhancers, additional skin-conditioning agents, skin penetration enhancing agents, skin protectants, solvents, emulsifiers, surfactants, hydrotropes, thickening agents, solubilizing agents, sunscreens, sunblocks, ultraviolet light absorbers or scattering agents, sunless tanning agents, antioxidants, radical scavengers, chelating agents, sequestrants, anti-acne agents, anti-inflammatory agents, anti-androgens, depilation agents, desquamation agents/exfoliants, organic hydroxy acids, skin healing agents, vitamins and derivatives thereof, and natural extracts, humectants, anti-static agents, diluents, emollients, pearlescent aids, foam boosters, pediculocides, pH adjusting agents, viscosity adjusting agents, proteins, and aesthetic components such as colorants, pigments, dyes, opacifying agents, essential oils, astringents, external analgesics, skin soothing agents, and the like. This list of optional components is not meant to be exclusive, and other optional components can be used. Such other materials are known in the art. Nonexclusive examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993).

Protocol 1—The Delivery or Longevity Test (Indirect Application)

The following Protocols are provided for determining if a benefit agent delivery system increases the level of benefit agent deposited and/or prolong or increase its subsequently release from a substrate. A benefit agent delivery system falls outside the scope of the present invention when it fails all of the following test protocols. For the purpose of illustration, perfume raw materials are used as the benefit agents and the benefit agent delivery system is a perfume delivery system (e.g., a perfume polymeric particle) in the following Protocols. More details of the Test Protocols using perfume or perfume raw materials are described in the co-filed patent application entitled "Perfume Polymeric Particles" in the name of Jordan et al. (P&G Case 9083M&).

Protocol IA (Perfume Accord Delivery or Longevity Test): The perfume delivery system of the present invention include polymer particles that enhance/increase the level of perfume raw materials (PRMs) deposited onto and/or subsequently released from a substrate; the polymer particles may be selected to have an affinity for perfume raw materials having a Kovats Index value of less than about 1700, preferably from about 1000 to about 1400. Multiple PRMs, available in the form of commercial perfume accord, may be tested together in the presence of a single or multiple polymer particles, as long as the analytical measurements (such as chromatography) are not affected by such combination. Typically, when the concentration of the PRMs are within a factor of about 10, the measurements do not appear to be affected by the presence of other PRMs in the same test. A fabric article in an aqueous medium is used as the substrate for purposes of this test protocol.

a) Concentration of PRM(s) and PP(s) in the Test Solution

The concentrations of PRMs and PP to be used in the Longevity Test (LT) are the lowest concentrations, in a series of solutions prepared from an initial test solution ($TS_0$), at which each PRM in the test solution is detected in the headspace sample collected from the treated substrate at one or more of the designated time points. If this condition is not met by $TS_0$, the concentrations of PRMs and PP in the test solution are doubled and the new solution ($TS_1$) is tested in the same manner. The process is repeated until the above PRM detection condition is met. The concentrations of PRMs and PP in the test solution ($TS_n$) that meets the above PRM detection condition relate to the concentrations of the PRMs and PP in $TS_0$ according to the following equation:

$$[PRM, PP] \text{ in } TS_n = 2^n [PRM, PP] \text{ in } TS_0; \text{ where } n = 0, 1, 2, 3 \ldots$$

In some instances, the process of doubling the concentration is repeated until the concentration of the PRMs and of PP both exceed 5% by weight of the test solution and the above PRM detection condition is still not met. Then, the following alternatives may be used in conducting the test. The aliquot of $TS_n$ transferred onto the substrate is increased from 1.0 mL to 3 mL, then to 10 mL, or the substrate size is increased to 1.0 g, 3 g, then to 10 g, until (i) the above PRM detection condition is met, or (ii) with respect to individual PRM that has a concentration greater than 0.1 wt % of the perfume, at least one of the following two alternative conditions is met:

(1) at least 80% of the low KI PRMs in the test solution and at least 80% of high KI PRMs in the test solution are detected in the headspace sample collected from the treated substrate at one or more of the designated time points; or (2) at least 10 of the low KI PRMs in the test solution and at least 5 of the high KI PRMs in the test solution are detected in the headspace sample collected from the treated substrate at one or more of the designated time points.

b) The Test Procedure

The test solution is prepared by dissolving or mixing PRM (s) and PP(s) are separately added into a composition at concentrations equal to those used in a consumer product, such as a laundry detergent. For example, the respective concentration of PRM(s) and PP(s) in a consumer product may be 2.0% and 4.0% by weight of the product. The mixture is thoroughly mixed so that it is visually uniform. The, the mixture is closed to the atmosphere and aged for 24 hours at room temperature to obtain the initial test solution, designated $TS_0$.

A 4 cm diameter fabric circle, weighing 0.45 to 0.65 g, is cut from an 86/14 cotton/poly terry wash cloth (obtained from EMC, 7616 Reinfold Drive, Cincinnati, Ohio 45237) and used as the test substrate. The weights of substrates in a given test should be within ±0.02 g of one another. A 1.0 mL aliquot of $TS_0$ is transferred by a pipette onto the substrate, with the pipette pointing close to the center of the substrate. Then, a 1.0 mL aliquot of deionized (DI) water is added to the substrate in the same manner. The substrate is lathered by rubbing against the palm of a nitrile-gloved hand for 1 minute. The substrate is then placed in a bottle containing 40 mL of 35° C. DI water; the bottle is capped and shaken for 30 seconds. The substrate is then removed using forceps and gently blotted on paper towels to remove excess water. The substrate, treated by the above steps (including charging with test solution, diluting, lathering/washing and rinsing) is left open to the atmosphere under ambient conditions to air dry for the specified period of time. Subsequently, the substrate is analyzed via headspace gas chromatography (HSGC) to determine the amount of each perfume raw material in the headspace at each of the following times: 2, 6 and 24 hours.

c) Headspace Gas Chromatography (HSGC)

A suitable equipment is described by S. Maeno and P. A. Rodriguez in J. Chromatography, vol. A731 (1996) pages 201-215. The equipment includes:

1) a headspace collector to contain the substrate (treated and air dried as described above) and allow PRM(s) to partition into the headspace and reach equilibrium;

2) a trap containing a porous polymer, which has the ability to retain aroma materials (e.g., perfume or perfume raw materials);

3) a transfer device to transfer the trapped headspace vapors onto a GC for quantitative analysis; and 4) GC-MS with headspace detection capabilities, and uses helium as the mobile phase.

A substrate, which has been treated and air dried for a specified time period as described above, is placed in a headspace collector and allowed to partition and reach equilibrium, which takes about two hours. After equilibration, a trap containing a porous polymer having the ability to retain aroma materials, preferably Tenax® TA 35/60 mesh (available from Gerstel, Inc., Baltimore, Md.), is operatively connected to the headspace collector to capture the equilibrated headspace vapors. A transfer device is used to transfer the trapped headspace vapors, which contains perfume raw materials, onto a GC for quantitative analysis. This device is able to heat the porous polymer trap containing the collected headspace vapors, and transfer the vapors to a cold trap cooled to lower than about −100° C. (generally by liquid nitrogen). Following complete transfer to the cold trap, the cold trap is flash heated in a short period of time, typically about 1 minute, to a temperature of about 280° C., resulting in the transfer of the headspace vapors directly onto a capillary GC column.

A typical column is a 30-60 meters long with an inner diameter of 0.18-0.32 mm, with a stationary phase, which can be, 100% dimethylpolysiloxane (a DB-5 column) or phenylmethylpolysiloxane containing about 5% phenyl. The GC-MS has the capability of identifying and quantifying PRMs of the aldehyde- or ketone-type. Identification is accomplished via Mass Spectrometry and quantification is performed using a separate detector, such as an FID (flame ionization) detector or PID (photo ionization) detector. Specific GC/MS conditions are described below.

The perfume components are separated on a DB-5 column (dimethylsiloxane, 60 m×0.32 mm, 0.25 μm) in split mode to both an MS (for identification) and FID (for quantitation). GC conditions are as following: the sample is held at oven temperature of about 35° C. for 2 min, then the GC is programmed to ramp up to 200° C. at 4° C./min, followed by a ramp to 325° C. at 10° C./min. Inlet pressure is kept constant at 13.7 psi (9.45 $N/m^2$), which is equivalent to an inert gas (e.g., helium) flow of about 2.4 mL/min. MS conditions are as following: scan range 35 to 400 amu (atomic units). Transfer line is maintained at about 250° C.

The quantitative measurements should be reproducible to within 20% of the average from the runs. If the result from a given run is not within said range, the data from said run should be discarded and the test repeated. The average of at least 3 satisfactory runs is reported.

d) Exemplary Results

A suitable test solution $TS_n$ meeting the PRM detection condition or alternative condition(s) described above is prepared. A second test solution $TS_c$ is prepared containing all the components at the same concentrations as in $TS_n$ except that the polymer particles have been removed. $TS_c$ serves as the control solution in the test. Data are gathered for a given test solution (either $TS_c$ or $TS_n$) as described above and analyzed via headspace gas chromatography (HSGC) to determine the amount of each benefit agent in the headspace at each of the following three designated times: 2, 6 and 24 hours.

A longevity benefit is confirmed for a particular PRM/PP delivery system when the quantitative amount of the PRM in the headspace collected from the substrate treated with $TS_n$ at any one of the three designated times points is greater than the amount of the same PRM in the headspace collected from the substrate treated with $TS_c$ at the corresponding time point.

The Longevity Test results can be reported as the Response Factor (RF), which is the ratio of the amount of benefit agent (e.g., perfume raw material) in the headspace collected from a substrate treated with $TS_n$ at a specific time point, compared to the amount of the same benefit agent in the headspace collected from a substrate treated with $TS_c$ at the same time point. A benefit agent delivery system falls with in the scope of the present invention when its RF is at least about 1.5, preferably at least about 3, and more preferably at least about 5, and most preferably at least about 10.

The following table demonstrates the type of results that can be obtained from a Longevity Test. The data confirms a greater longevity benefit for $PRM^1$ and $PRM^2$ compared to $PRM^3$ and $PRM^4$ (at t=24 h, the area count from $TS_n > TS_c$).

Longevity Test (Time = 24 h):

| PRM | KI | Area Count $TS_c$ | Area Count $TS_n$ | RF |
|---|---|---|---|---|
| 1 | 1033 | 38,000 | 418,000 | 11x |
| 2 | 1122 | 55,000 | 275,000 | 4.1x |
| 3 | 1770 | 110,000 | 143,000 | 1.3x |
| 4 | 1893 | 10,000 | 12,000 | 1.2x |

Alternatively, a perfume delivery system falls within the scope of the present invention when the Response Factor ($RF_{LKI}$) reported for any perfume raw material having a Kovats Index between about 1000 and 1400 is greater than the Response Factor reported for any perfume raw material having a Kovats Index greater than about 1700 ($RF_{HKI}$). In other words, a perfume delivery system falls within the scope of the present invention when the ratio $RF_{LKI}/RF_{HKI}$ is at least about 1.2, preferably at least about 3, and more preferably at least about 5, and most preferably at least about 10.

Further, a perfume delivery system falls within the scope of the present invention when the Average Response Factor ($ARF_{LKI}$) reported for all measured perfume raw material having a Kovats Index between about 1000 and 1400 is greater than the Average Response Factor ($ARF_{HKI}$) reported for all measured perfume raw materials having a Kovats Index greater than about 1700. Specifically, a perfume delivery system falls within the scope of the present invention when the ratio $ARF_{LKI}/ARF_{HKI}$ is at least about 1.2, preferably at least about 3, and more preferably at least about 5, and most preferably at least about 10.

Protocol IB (Selected Perfume Raw Material Accord): Each benefit agent delivery system comprising a polymer particle is tested in accordance with Protocol IB, in which an accord, made of selected perfume raw materials, is tested with each polymer particle (PP) to determine if the combination of PRMs and PP(s) demonstrates an enhancement or increase in the level of PRM(s) delivered to or released from a substrate, or a sustained release time, compared to that obtained for the PRM alone. The selected PRM accord is used to prepare test solutions ($TS_a$ and $TS_c$) and tested in the manner as described above in Protocol IA.

Since the polymeric particles of the present invention should desirably have enhanced affinity for low KI PRMs (i.e., top notes), it can be expected that a low KI PRM may be non-detectable in $TS_c$ and becomes detectable in $TS_n$, which indicates that an enhanced delivery of said PRM to the substrate is achieved when the polymeric particle is present; in this situation, the Response Factor value for such low KI PRM shall be defined as 10×. However, if a high KI PRM is non-detectable in $TS_c$ and becomes detectable in $TS_n$, result form such high KI PRM shall be excluded from the analysis. If any of the 20 PRMs exhibits an HSGC area count in $TS_n$ (the sample solution) that is less than the HSGC area count in $TS_c$ (the control solution), the Response Factor value for such PRM(s) shall be defined as 1.0×.

The perfume delivery system falls within the scope of the present invention when the Average Response Factor (ARF) reported for the following 10 Low Kovats Index PRM standards is greater than the Average Response Factor (ARF) reported for the following 10 High Kovats Index PRM standards. Specifically, the ratio of $ARF_{LKI}/ARF_{HKI}$ is at least about 1.2, preferably at least about 2, and more preferably at least about 4. Moreover, this ratio also demonstrates a selectivity or affinity of the polymeric particles for low KI PRMs than high KI PRMs.

| Low KI (LKI) | | | |
|---|---|---|---|
| limonene | 1033 | 138-86-3 | 136.1 |
| benzyl alcohol | 1037 | 100-51-6 | 108.1 |
| dihydromyrcenol | 1072 | 18479-58-8 | 156.2 |
| methyl benzoate | 1081 | 93-58-3 | 136.1 |
| Linalool | 1100 | 78-70-6 | 154.1 |
| phenyl ethyl alcohol | 1122 | 60-12-8 | 122.1 |
| citronellal | 1155 | 106-23-0 | 154.1 |
| benzyl acetate | 1164 | 140-11-4 | 150.1 |
| citronellol | 1237 | 106-22-9 | 156.2 |
| Citral | 1254 | 5392-40-5 | 152.1 |
| High KI (HKI) | | | |
| PRM | KI Value | CAS # | MW |
| hexyl cinnamic aldehyde | 1770 | 101-86-0 | 216.2 |
| benzyl benzoate | 1791 | 120-51-4 | 212.1 |
| cedryl acetate | 1811 | 77-54-3 | 264.2 |
| phenyl ethyl benzoate | 1887 | 94-47-3 | 226.2 |
| galaxolide | 1893 | 1222-05-5 | 258.2 |
| benzyl salicylate | 1904 | 118-58-1 | 228.1 |
| phenyl ethyl phenyl acetate | 1945 | 102-20-5 | 240.1 |
| Geranyl benzoate | 1985 | 100012-96-0 | 258.2 |
| phenyl ethyl salicylate | 1987 | 87-22-9 | 242.1 |
| Ethylene brassylate | 2060 | 105-95-3 | 270.2 |

Protocol II (Direct Applications): The same procedure is followed as with indirect application, with the modifications (1) the aliquot of $TS_0$ is added to the substrate and the substrate does not receive the subsequent dilution with water or rinse; and (2) the time points at which the test results are evaluated include a fourth time point at 7 days.

A longevity benefit is confirmed for a particular polymer particle (PP) when the quantitative amount of any PRM in the headspace from $TS_n$ at any one of the four designated time points is greater than the amount of the same PRM in the headspace from $TS_n$ at the corresponding time point.

In one embodiment where the perfume delivery system is used in a direct application mode (such as in a leave-on product), the polymer particle in the perfume delivery system may "flatten" the release profile of the PRMs. That is, the initial blooming of PRMs is reduced/suppressed and the PRMs are, instead, released from the perfume release system in a controlled, extended manner over time. The suppression of initial blooming can result in the initial headspace count of a PRM released from a substrate treated with $TS_n$ (containing PRM and PP) at a short time point (e.g., from about 30 minutes to about 1 hour) to be lower than the headspace count of a PRM released collected from a substrate treated with $TS_c$ (containing PRM without PP) at the corresponding time point. At later time points however, the longevity benefit is observed. Preferably, the polymer particles of the present invention increase the longevity of PRMs having a Kovat Index of less than 1700, and more preferably increase the longevity of PRMs having a low Kovat Index, which is from about 1000 to about 1400, to a greater extent than PRMs have a high Kovat Index, which is greater than about 1700.

The following table demonstrates the type of results that can be obtained from a Longevity Test with Direct Applications. The data confirms a longevity benefit for $PRM^1$ (at t=6 hours, the area count from $TS_n > TS_c$) and $PRM^2$ (at t=2 and 6 hours, the area count from $TS_n > TS_c$) in the presence of polymer particle (PP).

| | HSGC Area Count for Benefit Agent with and without PP | | | | | |
|---|---|---|---|---|---|---|
| Time | $PRM^1$ (KI = 1033) | | $PRM^2$ (KI = 1122) | | $PRM^3$ (KI = 1770) | |
| (h) | $TS_c$ | $TS_n$ | $TS_c$ | $TS_n$ | $TS_c$ | $TS_n$ |
| 2 | 3000 | 2500 | 20 | 1000 | 850 | 700 |
| 6 | 750 | 1500 | ND | 150 | 25 | ND |
| 24 | ND | 50 | ND | ND | ND | ND |

ND = Not detected.

Protocol III Affinity Test

The polymer particles useful in the perfume delivery system of the present invention exhibit greater affinity for a PRM, which has one or more of the following characteristics: a molecular weight of less than about 200; a boiling point of less than about 250° C.; a ClogP of less than about 3; or a Kovats Index value of less than about 1700, preferably from about 1000 to about 1400, than its affinity for other PRMs having none of these characteristics. The following Polymer particle Affinity Test Protocol III can be used to determine if a polymer particle falls within the scope of the present invention.

The polymer particles are thoroughly mixed (via stirring, shaking, and the like) in a liquid consumer product containing perfume (e.g., a commercially available liquid fabric softener typically contains perfume). The product and polymer particles are allowed to equilibrate (e.g., for 34 days), during which the polymer particles become associated (or "loaded") with one or more of the PRMs in the perfume. Then, the product and loaded polymer particles are separated via ultra centrifugation at 40,000 rpm for 16 hours. Subsequent to centrifugation, the contents separate into distinguishable layers, e.g. a lipid layer on top, an aqueous layer in the middle, and a particle layer on the bottom. A sample from each layer is extracted with a suitable organic solvent (e.g. acetone) and analyzed via GC/MS for perfume identification using the instrument conditions given above.

The selectivity or affinity of the polymer particle, as shown in the GC/MS analysis results, is demonstrated when the bottom particle layer is relatively enriched in PRMs fitting the above criteria of Kovats Index value, molecular weight, boiling point, and/or ClogP, compared to the concentrations of the same PRMs in either of the top or middle layer. In other words, the ARF of the low KI PRMs in the bottom particle layer is at least about 1.2×, preferably at least about 4×, higher than the ARF of the low KI PRMs in the top or middle layer.

Benefit Agent Delivery System And Product Preparation The benefit agent delivery system comprising the polymer particles and the benefit agents is prepared by the separate addition mode wherein the polymer particle and the benefit agent are separately added to a product matrix (a liquid or a granule) in a manner similar to adding an ingredient to the product matrix in preparing the final product formulation. In the separate addition mode, the formation of the benefit agent delivery system is facilitated by the polymer particle's affinity for the benefit agent it is designed for. Thorough mixing is frequently carried out using high shear agitation. A gentle heating to about 40° C. to about 65° C. may be used. Essential or adjunct ingredients may be added to the matrix at any time, with respect to the addition of the benefit agent and the polymer particle, to form the complete end product.

Cleaning and Fabric Treatment Products

The benefit agent delivery systems of the present invention are preferably incorporated into a wide variety of cleaning products and fabric treatment products. Such products include both laundry and cleaning compositions which are typically used for laundering fabrics and cleaning hard surfaces such as dishware, floors, bathrooms, toilet, kitchen and other surfaces in need of a prolonged or delayed release of the benefit agent. That is, laundry and cleaning compositions of the present invention include not only detergent compositions that provide fabric cleaning benefits, but also cleaning compositions that provide hard surface cleaning benefit. Additionally, compositions containing the delivery systems of the present invention also include fabric treatment or finishing products, such as fabric softeners or fabric enhancers.

Products incorporating the benefit agent delivery systems of the present invention also include personal care products that deliver a benefit to skin, hair and/or nail. Such product may be used to provide cleaning benefits to substrates in the form of shampoos or body wash compositions or to provide non-cleaning benefits to the substrates in the form of hair conditioners or skin lotions.

In a specific embodiment, wherein the benefit agents comprise perfumes, the effectiveness of the delivery to treated surfaces of this benefit agent can be quantified by a parameter called the Dry Surface Odor Index. Determination of such a parameter is fully described in PCT Application No. WO 00/02982. Preferably, when the perfume delivery systems are incorporated into cleaning and fabric treatment products, a Dry Surface Odor Index of more than about 5 and preferably at least about 10 is achieved. In other embodiments, the perfume delivery systems will provide a desirable change in the display or character of the perfume on the substrate surface without necessarily providing an increase in the Dry Surface Odor Index.

In general, the benefit agent delivery systems herein can be incorporated into cleaning or fabric treatment products herein such that levels of polymer particle plus benefit agent range from about 0.005% to 20%, more preferably from about 0.05% to 10%, even more preferably from about 0.1% to 5% by weight of the product composition. For cleaning products, the polymer particle plus benefit agent combination will generally be incorporated at concentrations of from about 0.005% to 10%, along with from about 1% to 50% by weight of the product composition, of a surfactant. For fabric treatment products, the polymer particle/benefit agent combination will generally be incorporated at concentrations of from about 0.05% to 10% by weight of the product composition, along with from about 1% to 50% by weight of the product composition, of a fabric softening or treating agent.

In specific embodiments of the present invention, the perfume polymeric particles can be formulated into fabric laundering products to achieve formulation compatibility and stability therein. The fabric laundering compositions may include a deposition polymer to facilitate the deposition of the perfume polymeric particles. These deposition polymers may be anionic, cationic, nonionic and/or zwitterionic. When the polymer particles comprise anionic monomers, the deposition polymer for laundering compositions is preferably cationic.

EXAMPLES

Preparation of the benefit agent delivery systems herein and their incorporation into certain types of cleaning products can be illustrated by the following examples:

Example I

Preparation of Liquid Detergent Composition

A heavy-duty liquid detergent composition in accordance with the present invention can be made as follows:

Step 1—a conventional heavy-duty liquid detergent composition is made by any conventional method known in the art;

Step 2—2% by weight of a polymer particle in accordance with the present invention is added to the composition from Step 1 and the composition is then mixed for about 1-3 minutes;

Step 3—0.15% by weight of a benefit agent in accordance with the present invention is added to the polymer particle composition from Step 2 and the composition is then mixed for about 5 minutes.

*Note that Step 2 and Step 3 are separate discrete addition steps.

Example II

Preparation of Personal Cleansing Composition

A personal cleansing composition in accordance with the present invention can be made as follows:

Step 1—the surfactants (components 1-4 in the Table below), EDTA, trihydroxystearin, and lauric acid are mixed in a container and heated to 190° F. (87.8° C.) and allowed to cool; when the temperature drops below 140° F. (60° C.), the glydant is mixed in;

Step 2—in a separate container, the cationic deposition polymer (7, 8) is completely hydrated in the water until the solution is clear and viscous;

Step 3—the polymer particle (such as Allianz® OPT) is added to the mixture prepared in step 2, and mixed until homogeneous; the benefit agent (such as perfume or perfume raw materials) is then added to the container and mixed; and Step 4—the pre-made surfactant mixture from the step 1 is added to the container from step 3 and the entire batch is mixed well until smooth; the pH is then adjusted to 6.3 and Sodium Sulfate is used to adjust the viscosity to between 7000 cps (7 Pa·s) and 10,000 cps (10 Pa·s).

Personal Care Composition Examples

| | Component (wt %) | 1 | 2 | 3 | 4 |
|---|---|---|---|---|---|
| 1 | Sodium lauryl ether 2EO sulfate | 7 | 7 | 7 | 7 |
| 2 | Cocoamidopropyl Betaine | 2 | 2 | 2 | 2 |
| 3 | Sodium Lauroyl Sarcosinate | 2 | 2 | 3 | 3 |
| 4 | Sodium Lauryl Sulfate | 3 | 3 | 3 | 3 |
| 5 | Polymer particle - Allianz ® OPT | | 5 | 5 | |
| 6 | Polymer particle - cationic | | | | 5 |
| 7 | Glydant ® | 0.21 | 0.21 | 0.21 | 0.21 |
| 8 | Ucare ® KG-30 M | 0.35 | 0.35 | | |
| 9 | Nhance ® 3169 | | | 0.25 | |
| 10 | Carboxy Methyl Cellulose | | | | 0.1 |
| 11 | Water | balance | balance | balance | balance |
| 12 | Sodium Sulfate | 1 | 1 | 1 | 1 |
| 13 | Citric Acid | Adjust pH | Adjust pH | Adjust pH | Adjust pH |
| 14 | EDTA | 0.15 | 0.15 | 0.15 | 0.15 |
| 15 | Trihydroxystearin | 1.5 | 1.5 | 1.5 | 1.5 |
| 16 | Lauric Acid | 0.5 | 0.5 | 0.5 | 0.5 |
| 17 | Perfume | 2 | 2 | 2 | 2 |

Allianz ® is available from Allianze Corp., Los Angeles, CA;
Glydant ® is available from Glycol Chemicals, Inc., Greenwich, CT;
Ucare ® is available from Union Carbide Corp., Danbury, CT; and
Nhance ® is available from Harris Research Inc., Logan, UT.

Example III

Preparation of Personal Cleansing Composition

A personal cleansing composition in accordance with the present invention can be made as follows:

Step 1—the surfactants (components 1-4), EDTA, trihydroxystearin, and lauric acid are mixed in a container and heated to 190° F. (87.8° C.) and allowed to cool; when the temperature drops below 140° F. (60° C.), the glydant is mixed in;

Step 2—in a separate container, the cationic deposition polymer (7, 8) is completely hydrated in the water until the solution is clear and viscous;

Step 3—the pre-made surfactant mixture from the step 1 is added to the container from step 2 and the entire batch is mixed; the benefit agent (such as perfume or perfume raw materials) is then added to the container and mixed; and Step 4—polymer particle (such as Allianz® OPT) is added to the mixture prepared in step 3, and mixed; the pH is then adjusted to 6.3 and Sodium Sulfate is used to adjust the viscosity to between 7000 cps (7 Pa·s) and 10,000 cps (10 Pa·s).

All documents cited, including the priority document, are, in relevant part, incorporated herein by reference; the citation of any document is not to be construed as an admission that it is prior art with respect to the present invention.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A non-encapsulated benefit agent delivery system suitable for delivering a benefit agent to a substrate, the benefit agent delivery system comprising an aqueous dispersion of from about 0.002% to about 0.05%, by weight, of a water-insoluble polymer particle and from about 0.001% to about 10%, by weight, of a benefit agent, wherein the polymer particle has a glass transition temperature from about 50° C. to about 120° C. and is a polymer of vinyl acetate and vinyl pyrrolidone at a weight ratio of vinyl acetate: vinyl pyrrolidone in the range of about 10:0.02 to about 5:2.5 and the polymer and the benefit agent are non-polymerically associated; and when the benefit agent delivery system is deposited onto the substrate, directly or indirectly, the Response Factor (RF) exhibited by the benefit agent delivery system is at least about 1.5, as measured by Test Protocol I or II, wherein said benefit agent is a member selected from the group consisting of top note perfume raw materials and perfume accords having a Kovats Index of from about 1000 to about 1400; said dispersion comprising a colloidal stabilizer; said dispersion having a viscosity in a range of between 7000-10000 cps.

2. The delivery system according to claim 1 wherein the polymer particle comprises a polymer having a first affinity for a low Kovats index (LKI) perfume raw material having a Kovats Index of from about 1000 to about 1400 and a second affinity for a high Kovats index (HKI) perfume raw material having a Kovats Index of greater than about 1700, the first affinity is at least about 2 times greater than the second affinity, as measured by Affinity Test Protocol III.

3. The delivery system according to claim 1 wherein the benefit agent is a perfume accord comprising one or more LKI perfume raw materials, each having a Kovats Index value of from about 1000 to about 1400, and one or more HKI perfume raw materials, each having a Kovats Index value of greater than about 1700.

4. The delivery system according to claim 3 wherein the LKI perfume raw materials collectively provide a first Average Response Factor ($ARF_{LKI}$) and the HKI perfume raw materials collectively provide a second Average Response Factor ($ARF_{HKI}$); the perfume polymeric particle has a ratio of $ARF_{LKI}$ / $ARF_{HKI}$, of at least about 1.2.

5. A composition comprising the benefit agent delivery system according to claim 1 and an adjunct ingredient.

* * * * *